[19] United States Patent
Cooper

[11] 4,388,477
[45] Jun. 14, 1983

[54] HYDROFORMYLATION PROCESS EMPLOYING UNMODIFIED RHODIUM-COBALT CATALYST

[75] Inventor: James L. Cooper, Longview, Tex.

[73] Assignee: Eastman Kodak Company, Rochester, N.Y.

[21] Appl. No.: 269,094

[22] Filed: Jun. 2, 1981

[51] Int. Cl.$^3$ ............................................. C07C 45/50
[52] U.S. Cl. .................................. 568/451; 568/452; 568/909
[58] Field of Search ............... 568/451, 452, 453, 454, 568/455, 456, 909, 882, 883

[56] References Cited

U.S. PATENT DOCUMENTS

| | | | |
|---|---|---|---|
| 2,880,241 | 3/1959 | Hughes | 568/451 |
| 3,527,809 | 9/1970 | Pruett et al. | 568/454 |
| 3,917,661 | 11/1975 | Pruett et al. | 568/454 |
| 3,965,192 | 6/1976 | Booth | 560/598 |
| 4,148,830 | 4/1980 | Pruett | 568/454 |
| 4,200,592 | 4/1980 | Hignett et al. | 568/455 |
| 4,205,013 | 5/1980 | Weber et al. | 568/451 |
| 4,278,819 | 7/1981 | Korff et al. | 568/454 |
| 4,306,085 | 12/1981 | Kim et al. | 568/454 |
| 4,306,086 | 12/1981 | Demay | 568/454 |

*Primary Examiner*—Werren B. Lone
*Attorney, Agent, or Firm*—Donald W. Spurrell; Daniel B. Reece, III

[57] ABSTRACT

Disclosed is a process for the hydroformylation of olefinic material in general, and more particularly concerns the hydroformylation of olefins of 2 to 20 carbons, preferably of 3 to 10 carbons for the production of relatively high proportions of branched aldehydes, comprising contacting olefinic material in a reaction zone at a temperature of from about 60° C. to about 250° C. and a pressure of from about 750 psig to about 10,000 psig with hydrogen, carbon monoxide, and a catalyst consisting of a mixture of unmodified cobalt and unmodified rhodium in a molar ratio range of from about 0.5 to about 100, wherein for each mole of olefin there is present from about $1 \times 10^{-7}$ to about $1 \times 10^{-5}$ moles of rhodium and from about $1 \times 10^{-7}$ to about $1 \times 10^{-4}$ moles of cobalt, for a sufficient period of time to permit reaction of the olefinic material with the carbon monoxide and hydrogen to form aldehyde product.

6 Claims, No Drawings

HYDROFORMYLATION PROCESS EMPLOYING UNMODIFIED RHODIUM-COBALT CATALYST

This invention concerns a hydroformylation process wherein one or more olefins and/or other unsaturated organic compounds may be converted to aldehydes for use as such or for conversion by known methods to products such as alcohols and acids. More particularly, the invention concerns an oxo process especially suited for the preparation of unusually high proportions of branched aldehydes from α-olefins, particularly isobutyraldehyde from propylene and mixed valeraldehydes from butene-1. The isobutyraldehyde may be converted, for example, to 2,2,4-trimethyl-1,3-pentanediol monoisobutyrate useful as a high boiling solvent and coalescing aid for paints, and the mixed valeraldehydes converted to acids useful as a cattle feed additive.

Heretofore, the principal emphasis for oxo processes has been the production of relatively high ratios of normal to branched aldehyde product, and to this end the catalyst, reactants, and reaction conditions have been selected to give these ratios. See, for example, U.S. Pat. Nos. 3,527,809; 3,917,661; 3,965,192; and 4,148,830. For such processes the catalyst is typically cobalt or rhodium complexed with such materials as carbonyl, phosphines and phosphites, the latter two types more commonly referred to as ligands. Also, U.S. Pat. No. 2,880,241 discloses the use of a mixture of nonligandized cobalt and rhodium catalysts wherein the cobalt to rhodium molar ratio is preferably at least about 100 and the molar ratio of catalyst to olefin is very high, i.e., from about 0.002 to 20. With the prior art processes, there is need for concern for the instability of the catalyst during distillation operations and various techniques have been developed to impart greater stability to the catalyst and also to restore its activity.

Objects, therefore, of the present invention are to provide a catalyst system which gives a relatively low normal to branched product ratio in high yield and which operates effectively at very low catalyst concentrations; and to eliminate the need for ligandizing or otherwise enhancing catalyst stability and for restoration of its activity.

These and other objects hereinafter appearing have been attained in accordance with the present invention through the discovery that very low concentrations of mixtures of unmodified cobalt and rhodium catalysts effectively promote the hydroformylation of olefins and other unsaturated materials to aldehydes, particularly in relatively low normal to branched product ratios, e.g., below about 1.5 for propylene feed, while retaining their catalytic activity throughout including the distillation, for unusually long periods without the need for special stabilization, air regeneration or the like.

The present invention is more particularly defined as a hydroformylation process comprising contacting at least one olefin having from 2 to 20 carbon atoms in a reaction zone at a temperature of from about 60° C. to about 250° C., preferably from about 125° C. to about 175° C., and a pressure of from about 750 psig to about 10,000 psig, preferably 2,000 to about 3,000 psig, with hydrogen, carbon monoxide, and a catalyst consisting of a mixture of from about $10^{-7}$ to about $10^{-4}$ moles of unmodified cobalt and from about $10^{-7}$ to about $10^{-5}$ moles of unmodified rhodium per mole of olefin, said cobalt and rhodium being present in a molar ratio range of from about 0.5 to about 100, preferably 1.0 to about 20.0, and most preferably from about 4 to about 6, for a sufficient period of time to permit reaction of said olefin with said carbon monoxide and hydrogen to form aldehyde product.

An overflow reactor design is preferred for the present process, the catalyst leaving the reaction zone with the product aldehyde. The product solution is passed through a series of vapor liquid separators, the gases being recycled to the reactor, and the liquid let down to atmospheric pressure by conventional techniques. The mixture of aldehydes, solvent, and catalyst is then passed through a distillation column to remove aldehydes overhead, and the catalyst with high boiling base effluent is recycled back to the reactor. Conventional azeotropic and dry distillation techniques are suitable in the present process but it is preferred to carry out the distillations below about 120° C. The catalyst components are charged preferably with solvent to the reactor through suitable pressure, pumping means, preferably in their soluble forms, e.g., their carboxylate salts from acids derived from the product aldehydes, or as mineral acid salts or the like well known to the art as disclosed, for example, in the aforesaid U.S. Pat. No. 2,880,241.

In the process the syn gas is introduced into the reactor in a continuous manner by means, for example, of a primary compressor, and the ratio of hydrogen to carbon monoxide in the feed may be selected according to the particular olefin being hydroformylated and the reaction conditions present, as is well known in the art. Generally, the molar ratio of hydrogen to carbon monoxide in the reactor is maintained within the range of above about 0.5 to about 4.0, but it has been found in many hydroformylations that the rate of reaction as well as yield of the desired product may be increased by increasing the hydrogen to carbon monoxide molar ratio above 4.0, and up to about 10.0 or more. The syn gas preferably is present in a molar excess (total moles of $H_2 + CO$) with respect to the olefin and the molar ratio may vary typically from about 0.5 to about 20, preferably from about 1.2 to about 6.

The olefin is fed to the reactor by means of suitable pumps capable of operating under substantial pressures and the feed rates of the olefin and syn gas are selected to maintain the above recited molar ratios of these reactants in the reactor. Typical useful olefins include α-olefins containing from 2 to 20 carbon atoms and preferably from 3 to 10 carbon atoms, straight-chain or branched-chain, and optionally containing groups or substituents which do not interfere with the hydroformylation process. Illustrative such α-olefins are ethylene, propylene, 1-butene, 2-methyl propylene, 2-methyl-1-butene, 1-pentene, 1-hexene, 1-heptene, 1-octene, 2-ethyl-1-hexene, 1-dodecene and 1-octadecene. Also useful in the present process are the internal olefins such as butene-2 and cyclic olefins such as cyclooctene. If desired, mixtures of olefins can be fed to the reactor.

Any suitable solvent which does not adversely effect the process and which is inert with respect to the catalyst, olefin feed, syn gas and the hydroformylation products may be used. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents include 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the distillation column.

The invention will be illustrated further by the following examples although it will be understood that these examples are included merely for purposes of illustration and are not intended to limit the scope of the invention.

EXAMPLE 1

This example demonstrates the activity of rhodium in a typical propylene hydroformylation run.

Propylene (1 mole) was placed in a high pressure reactor which contained TMPDMI and 1 ppm (0.1 mg) of rhodium as the isobutyric acid salt. This corresponds to $1 \times 10^{-6}$ moles of rhodium per mole of olefin feed. A mixture of carbon monoxide and hydrogen (1 to 1) was pressured at 2,000 psig into the reactor and the temperature raised to 150° C., the pressure increasing to 2,500 psig. Gas uptake over the 30-minute reaction time was uniform. Chemical analysis showed 99 percent of the product was aldehyde. A linear to branched ratio of 0.97 was obtained at a production rate of 34.4 pounds per cubic foot-hour.

EXAMPLE 2

This example demonstrates that at the low cobalt concentrations utilized within the scope of the present invention, cobalt catalyst is incapable of catalyzing the hydroformylation reaction.

Propylene (1 mole) was placed in a high pressure reactor which contained TMPDMI and 10 ppm (1.0 mg) of cobalt was charged as the isobutyric acid salt. This corresponds to $1.7 \times 10^{-5}$ moles of cobalt per mole of olefin feed. A mixture of carbon monoxide and hydrogen (1 to 1) was pressured at 2,000 psig into the reactor and the temperature raised to 150° C., the pressure increasing to 2,500 psig. The reaction pressure was maintained at 2,500 psig throughout the 30-minute run time. A linear to branched ratio of 1.8 was obtained at a production rate of 0.26 pounds per cubic foot-hour.

EXAMPLES 3-9

These examples illustrate that under the reaction conditions of Example 1, the rhodium and cobalt mixed metal catalyst of the present inventions yields a reaction rate superior to the rhodium catalyst.

TABLE I

Effect of Cobalt Isobutyrate on the Oxo Activity of Rhodium Isobutyrate

| Example No. | Catalyst,[1] Co/Rh Molar Ratio | Production Rate,[2] lb/ft³-hr | Normal to Branched Ratio |
|---|---|---|---|
| 3 | 2 | 35.3 | 0.95 |
| 4 | 3 | 37.7 | 0.96 |
| 5 | 4 | 38.1 | 0.94 |
| 6 | 5 | 40.5 | 1.00 |
| 7 | 10 | 41.2 | 0.98 |
| 8 | 15 | 42.1 | 0.99 |
| 9 | 20 | 43.7 | 0.99 |

[1]Isobutyric acid salts of the cobalt and rhodium catalysts were employed for this process. Rhodium concentration in each run was 1 ppm by volume of reactor contents.
[2]Reaction conditions: 2,500 psig, synthesis gas (1/1), and 150° C.

EXAMPLE 10

This example illustrates the effect on the production rate and linear to branched ratio when using very high concentrations of cobalt in combination with low concentrations of rhodium. Propylene (1 mole) was charged to a high pressure reactor containing TMPDMI, 1 ppm (0.1 mg) of rhodium, and 400 ppm (40.0 mg) of cobalt both charged as the isobutyric acid salt. This corresponds to $1 \times 10^{-6}$ moles of rhodium per mole of olefin feed and $6.7 \times 10^{-4}$ moles of cobalt per mole of olefin feed. A mixture of carbon monoxide and hydrogen (1 to 1) was pressured at 2,000 psig into the reactor and the temperature raised to 150° C., the pressure increasing to 2,500 psig. Reactor pressure was maintained at 2,500 psig throughout the 15-minute run time. Chemical analysis showed 96 percent of the product was butyraldehyde with a linear to branched ratio of 1.56 and a production rate of 119 pounds per cubic foot-hour.

EXAMPLES 11-15

These examples demonstrate the thermal stability of the rhodium and cobalt mixed metal catalyst in reactor effluent from each of the propylene oxo runs of these examples which used 1 ppm of rhodium in each case and the amount of cobalt specified, the process conditions being those of Example 1. The effluent comprising a solution containing catalyst, butyraldehyde product, and TMPDMI was passed through a stainless steel circulating distillation column and the catalyst activity then checked by a propylene run according to the procedure of Example 1. The distillation is carried out as follows:

The reactor effluent is carefully transferred in the absence of air into the stainless steel distillation column to a level of 200 ml. The distillation is initiated by starting the base heater set at the desired temperature, reboiler circulation pump, and the base take off pump set at 600 ml/hr in concert with a column feed pump which pumps reactor effluent into the column at a rate to hold the column level at 200 ml. Butyraldehyde is distilled overhead and catalyst base product pumped into a lower 250 ml base product tank to bring the column to equilibrium, after which the base product (steady state) is collected in an upper 250 ml base product tank for the desired period. Approximately 200 ml of the steady state base product, hereinafter referred to as SSBP, is collected and the column shut down. For the azeotropic distillations water is fed to the column during the distillation at the desired rate. The column feed (CF) is analyzed by gas-liquid chromatography for TMPDMI by weight and for cobalt and rhodium/ml of CF. Gas liquid chromatographic and atomic absorption spectroscopic techniques have shown that no cobalt, rhodium or TMPDMI is distilled overhead.

For determining the amounts of CF and SSBP to be fed to the reactor for the catalytic activity evaluations, the SSBP of each particular example was analyzed chromatographically for TMPDMI by weight. Samples of SSBP were taken according to the relationship: mls of SSBP=(% TMPDMI in CF/% TMPDMI in SSBP)×mls of CF. It is noted that if no catalyst metals were lost during distillation, the CF and SSBP would have the same metal concentration.

TABLE II

Dry Butyraldehyde Distillations

| Ex. No. | Catalyst, Co/Rh Molar Ratio | Base Temp. °C. | Residence Time, min. | Prodn. Rate, lb/ft³-hr. CF | SSBP |
|---|---|---|---|---|---|
| 11 | Rh only | 120 | 20 | 50.7 | 25.5 |

TABLE II-continued

Dry Butyraldehyde Distillations

| Ex. No. | Catalyst, Co/Rh Molar Ratio | Base Temp. °C. | Residence Time, min. | Prodn. Rate, lb/ft³-hr. CF | SSBP |
|---|---|---|---|---|---|
| | (1 ppm) | | | | |
| 12 | 5.0 | 120 | 15 | 39.9 | 42.1 |
| 13 | 5.0 | 120 | 20 | 44.1 | 42.2 |
| 14 | 5.0 | 154 | 15 | 38.7 | 11.4 |
| 15 | 20.0 | 154 | 15 | 36.0 | 13.6 |

EXAMPLES 16-18

These examples further illustrate the utility of the rhodium and cobalt mixed metal catalyst during processing. Advantage is found in performing azeotropic distillations as a means of purifying oxo aldehydes. The following examples show that the mixed metal catalyst is stable to azeotropic distillation conditions.

TABLE II

Azeotropic Distillations

| Ex. No. | Catalyst, Co/Rh Molar Ratio | Water/ Feed Vol, % | Base Temp, °C. | Resid. Time, min. | Prodn. Rate, lb/ft³-hr. CF | SSBP |
|---|---|---|---|---|---|---|
| 16 | 5 | 0.5 | 120 | 15 | 37.0 | 39.0 |
| 17 | 5 | 6.0 | 120 | 20 | 34.9 | 34.4 |
| 18 | 5 | 20.0 | 95 | 20 | 45.8 | 45.6 |

The invention has been described in detail with particular reference to preferred embodiments thereof, but it will be understood that variations and modifications can be effected within the spirit and scope of the invention.

I claim:

1. A hydroformylation process comprising contacting at least one olefin having from 2 to 20 carbon atoms in a reaction zone at a temperature of from about 60° C. to about 250° C. and a pressure of from about 750 psig to about 10,000 psig with hydrogen, carbon monoxide, and a catalyst consisting of a mixture of unmodified cobalt and unmodified rhodium in a molar ratio of from about 0.5 to about 100, wherein for each mole of olefin there is present from about $1 \times 10^{-7}$ to about $1 \times 10^{-4}$ moles of cobalt and from about $1 \times 10^{-7}$ to about $1 \times 10^{-5}$ moles of rhodium, for a sufficient period of time to permit reaction of said olefin with said carbon monoxide and hydrogen to form aldehyde product.

2. The process according to claim 1 wherein said reaction zone is operated at temperatures between about 125° C. and 175° C. and at pressures between about 2000 psig and 3000 psig.

3. The process according to claim 2 wherein the molar ratio of cobalt to rhodium is from about 1.0 to about 20.

4. The process according to claim 3 wherein said olefin is selected from one or more of ethylene, propylene, 2-methyl propylene, 2-butene, 1-butene, 2-methyl-1-butene, 1-pentene, 1-hexene, 1-heptene and 1-octene.

5. The process according to claim 4 wherein the molar ratio of cobalt to rhodium is from about 4 to about 6.

6. The process according to claim 1 wherein reactor effluent containing the catalyst is subjected without prior stabilization to distillation below about 120° C. and the distillation base product is recycled to the reactor without reactivation treatment.

* * * * *